(12) United States Patent
    Bom

(10) Patent No.: US 10,178,875 B2
(45) Date of Patent: Jan. 15, 2019

(54) METHODS OF MODIFYING OR IMPARTING TASTE USING ORGANIC COMPOUNDS

(71) Applicant: Givaudan, S.A., Vernier (CH)

(72) Inventor: David C. Bom, Cincinnati, OH (US)

(73) Assignee: Givaudan S.A., Vernier (CH)

( * ) Notice: Subject to any disclaimer, the term of this patent is extended or adjusted under 35 U.S.C. 154(b) by 315 days.

(21) Appl. No.: 14/901,279

(22) PCT Filed: Jul. 1, 2014

(86) PCT No.: PCT/EP2014/063962
    § 371 (c)(1),
    (2) Date: Dec. 28, 2015

(87) PCT Pub. No.: WO2015/000900
    PCT Pub. Date: Jan. 8, 2015

(65) Prior Publication Data
    US 2016/0366922 A1    Dec. 22, 2016

Related U.S. Application Data

(60) Provisional application No. 61/841,602, filed on Jul. 1, 2013.

(51) Int. Cl.
    A23L 1/22      (2006.01)
    A23L 27/20     (2016.01)
    C07D 213/28    (2006.01)
    C07D 213/32    (2006.01)

(52) U.S. Cl.
    CPC ....... *A23L 27/2054* (2016.08); *A23L 27/2056* (2016.08); *C07D 213/28* (2013.01); *C07D 213/32* (2013.01); *A23V 2002/00* (2013.01)

(58) Field of Classification Search
    CPC ............. A23L 27/2054; A23L 27/2056; C07D 213/28; C07D 213/32; A23V 2002/00
    USPC .................. 426/534, 535, 536, 537, 650
    See application file for complete search history.

(56) References Cited

U.S. PATENT DOCUMENTS

| 2,615,892 | A  | 10/1952 | Clifford |
| 3,226,394 | A  | 12/1965 | Schipper |
| 3,574,221 | A  | 4/1971  | Hankovszky et al. |
| 7,476,399 | B2 | 1/2009  | Tachdjian et al. |
| 7,541,055 | B2 | 6/2009  | Dewis et al. |
| 7,888,470 | B2 | 2/2011  | Li et al. |
| 8,124,121 | B2 | 2/2012  | Tachdjian et al. |
| 8,404,455 | B2 | 3/2013  | Li et al. |

(Continued)

FOREIGN PATENT DOCUMENTS

| DE | 23 16 881 A1 | 4/1973 |
| EP | 1 291 342 A1 | 2/2003 |

(Continued)

OTHER PUBLICATIONS

PCT/EP2014/063962—International Search Report, dated Mar. 10, 2015.
PCT/EP2014/063962—International Written Opinion, dated Mar. 10, 2015.
PCT/EP2014/063962—International Preliminary Report on Patentability, dated Jan. 5, 2016.
GB1313696.5—British Search Report, dated Jan. 24, 2014.
Chemcats Accession No. 0090404185, Ambinter Stock Screening Collection, Publication Jan. 1, 2013, CAS Registry No. 298217-38-6.
Chemcats Accession No. 0072332306, Ryan Scientific Intermediate and Building Block Compounds, Publication Apr. 23, 2013, CAS Registry No. 1183541-70-9.

(Continued)

*Primary Examiner* — Leslie A Wong
(74) *Attorney, Agent, or Firm* — Curatolo Sidoti Co., LPA; Joseph G. Curatolo; Salvatore A. Sidoti

(57) ABSTRACT

A method of imparting to, or modifying in, a comestible product, umami taste, including the addition to a comestible product base of at least one compound of formula (I)

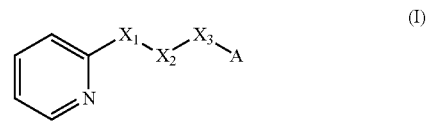

wherein one of $X_1$, $X_2$, or $X_3$ is selected from the group consisting of S, N and O and the remaining two are $CH_2$; and A is selected from

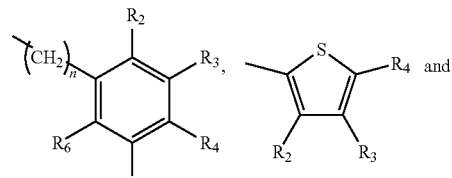 and 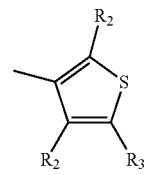

in which $R_1$, $R_2$, $R_3$, $R_4$ $R_5$, $R_6$ are independently selected from the group consisting of H, methyl, ethyl, propyl, OH, OMe, OEt, COOH, $COOR_7$, in which $R_7$ is selected from linear or branched $C_1$-$C_7$ alkyl, and $CONR_8R_9$, in which $R_8$ and $R_9$ are independently selected from hydrogen and straight or branched $C_1$-$C_4$ alkyl; or any two adjacent substituents $R_2$-$R_6$ together form a ring of 5 or 6 members; and n is 1 or 0.

16 Claims, No Drawings

(56) References Cited

U.S. PATENT DOCUMENTS

| | | |
|---|---|---|
| 8,735,081 B2 | 5/2014 | Li et al. |
| 8,895,050 B2 | 11/2014 | Tachdjian et al. |
| 9,091,686 B2 | 7/2015 | Li et al. |
| 9,173,424 B2 | 11/2015 | Wang et al. |
| 2005/0084506 A1 | 4/2005 | Tachdjian et al. |
| 2006/0068071 A1 | 3/2006 | Dewis et al. |
| 2006/0263411 A1 | 11/2006 | Tachdjian et al. |
| 2007/0104709 A1 | 5/2007 | Li et al. |
| 2008/0085994 A1 | 4/2008 | Li et al. |
| 2009/0111834 A1 | 4/2009 | Tachdjian et al. |
| 2011/0020517 A1 | 1/2011 | Rubin |
| 2011/0020518 A1 | 1/2011 | Delort et al. |
| 2011/0294981 A1 | 12/2011 | Li et al. |
| 2012/0100609 A1 | 4/2012 | Crawford et al. |
| 2012/0121783 A1 | 5/2012 | Wang et al. |
| 2012/0201763 A1 | 8/2012 | Tachdjian et al. |
| 2013/0030059 A1 | 1/2013 | Li et al. |
| 2013/0336892 A1 | 12/2013 | Li et al. |
| 2014/0295045 A1 | 10/2014 | Wang et al. |
| 2014/0342073 A1 | 11/2014 | Elings et al. |
| 2015/0084112 A1 | 3/2015 | Li et al. |
| 2015/0093339 A1 | 4/2015 | Tachdjian et al. |

FOREIGN PATENT DOCUMENTS

| | | |
|---|---|---|
| EP | 1 312 268 A1 | 5/2003 |
| EP | 1 642 886 A2 | 4/2006 |
| GB | 1 437 781 | 6/1976 |
| JP | 2000-351767 A | 12/2000 |
| WO | WO 03/088768 A1 | 10/2003 |
| WO | WO 2005/015158 A2 | 2/2005 |
| WO | WO 2006/003107 A1 | 1/2006 |
| WO | WO 2009/122316 A1 | 10/2009 |
| WO | WO 2009/122319 A2 | 10/2009 |
| WO | WO 2010/111713 A2 | 9/2010 |
| WO | WO 2011/004016 A1 | 1/2011 |
| WO | WO 2011/138266 A1 | 11/2011 |
| WO | WO 2013/041599 A1 | 3/2013 |

OTHER PUBLICATIONS

Lambrecht, et al., "Synthesis of Substituted Ethenylpryazines and Dialkylpridines and Their Sensory Properties", Flavor and Fragrance Journal, Apr. 4, 1997, pp. 439-442, vol. 12, John Wiley & Sons Ltd.

Profft, "Addition of Thiophenols and Thioether Ketones to 2-Vinylpyridine", Chemishe Technik, 1955, pp. 577-579, vol. 7, Leipzig, Germany. (CAS Abstract).

Profft, "Über die Darstellung von Thienyl-2.2'-äthylpyridyl-sulfiden", Wissenschaftliche Aeitschrift der Technischen Hochschule für Chemie Leuna-Merseburg, 1960, pp. 101-102.

Profft, "Über die Darstellung von Thienyl-2.2'-äthylpyridyl-sulfiden", Institut für Organische Chemie der Technischen Hochschule für Chemie Leuna-Merseburg, 1959, pp. 694-696.

Watanabe, et al., "Intramolecular Assistance of Electron Transfer from Heteroatom Compounds. Electrochemical oxidation of 2-(2-pyridyl)ethyl-substituted ethers, sulfides, and selenides", Bulletin of the Chemical Society of Japan, 2000, pp. 243-247, vol. 73, Issue 1. (CAS Abstract).

Office Action dated Mar. 14, 2017, for European patent application No. 14 734 162.2-1358.

Office Action dated Jan. 25, 2018, for European patent application No. 14 734 162.2-1106.

METHODS OF MODIFYING OR IMPARTING TASTE USING ORGANIC COMPOUNDS

CROSS REFERENCE TO RELATED APPLICATIONS

This application is a national stage application of International Application No. PCT/EP2014/063962, filed 1 Jul. 2014, which claims priority from U.S. Provisional Patent Application No. 61/841,602, filed 1 Jul. 2013, which applications are incorporated herein by reference.

This disclosure relates to the use of compounds that can impart or modify umami taste in comestible products.

Umami taste is an important flavour sensation. Accordingly, in the flavour industry there is a constant demand for compounds that impart or modify it.

Such compounds extend a flavourist's palette and result in greater product diversity for consumers. Furthermore, such compounds may replace, or reduce reliance, on compounds conventionally used to impart or modify these tastes e.g. monosodium glutamate (MSG), the use of which may be undesirable.

It has now been found that certain compounds), as defined herein, may be used to impart to, or modify in, a flavour composition or comestible product, umami taste.

There is therefore provided a method of imparting to, or modifying in, a flavour composition or comestible product, umami taste, comprising the addition to said flavour composition or comestible product of at least one compound of formula (I)

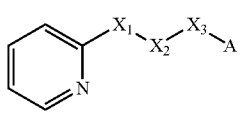
(I)

wherein:
one of $X_1$, $X_2$, or $X_3$ is selected from the group consisting of S, N and O and the remaining two are $CH_2$; and A is selected from

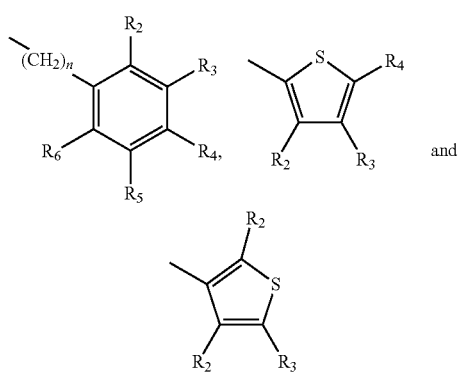

in which $R_1$, $R_2$, $R_3$, $R_4$ $R_5$, $R_6$ are independently selected from the group consisting of H, methyl, ethyl, propyl, OH, OMe, OEt, COOH, COOR$_7$, in which $R_7$ is selected from linear or branched $C_1$-$C_7$ alkyl, and CONR$_8$R$_9$, in which $R_8$ and $R_9$ are independently selected from hydrogen and straight or branched $C_1$-$C_4$ alkyl; or any two adjacent substituents $R_2$-$R_6$ together form a ring of or 6 members; and n is 1 or 0. The abbreviation Me represents —CH$_3$; Et represents —C$_2$CH$_3$.

In a particular embodiment, one of $X_1$, $X_2$, or $X_3$ is S and the remaining two are $CH_2$.

In a further particular embodiment, $X_1$ is S and $X_2$, and $X_3$ are $CH_2$.

In a further particular embodiment, $X_2$ is S and $X_1$, and $X_3$ are $CH_2$.

In a further particular embodiment, A is

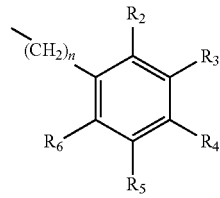

in which $R_1$, $R_2$, $R_3$, $R_4$ $R_5$, $R_6$ are independently selected from the group consisting of H, methyl, ethyl, propyl, OH, OMe, OEt, COOH, COOR$_7$, in which $R_7$ is selected from linear or branched $C_1$-$C_7$ alkyl, and CONR$_8$R$_9$, in which $R_8$ and $R_9$ are independently selected from hydrogen and straight or branched $C_1$-$C_4$ alkyl; or any two adjacent substituents $R_2$-$R_6$ together form a ring of 5 or 6 members; and n is 1 or 0.

In a further particular embodiment, $X_1$ is S and $X_2$, and $X_3$ are $CH_2$, and A is

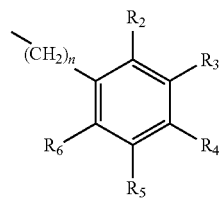

in which $R_1$, $R_2$, $R_3$, $R_4$ $R_5$, $R_6$ are independently selected from the group consisting of H, methyl, ethyl, propyl, OH, OMe, OEt, COOH, and COOR$_7$, in which $R_7$ is selected from linear or branched $C_1$-$C_7$ alkyl, and n is 0.

In a further particular embodiment, the compound of formula (I) is selected from the group consisting of:
2-(2-(Phenylthio)ethyl)pyridine, 2-(2-(Phenylthio)ethyl)pyridine hydrochloride, Methyl 4-((2-(pyridin-2-yl)ethyl)thio)benzoate hydrochloride, 2-(2-(p-tolylthio)ethyl)pyridine hydrochloride, 2-(2-(o-tolylthio)ethyl)pyridine hydrochloride, 4-((2-(pyridin-2-yl)ethyl)thio)phenol, 2-((2-(pyridin-2-yl)ethyl)thio)phenol, 2-(2-((3-methoxyphenyl)thio)ethyl)pyridine, Methyl 2-((2-(pyridin-2-yl)ethyl)thio)benzoate hydrochloride, 3-((2-(pyridin-2-yl)ethyl)thio)phenol, 2-(2-(benzylthio)ethyl)pyridine, 2-(2-(m-Tolylthio)ethyl)pyridine hydrochloride, and 2-(2-((4-Methoxyphenyl)thio)ethyl)pyridine hydrochloride.

A compound of formula I may be used in the form as shown above, or in its ionic form with or without a counter-ion (in the form of its salt), for example it may be used in the form of its sodium, potassium, calcium, ammonium, chloride, hydrochloride, sulphate, phosphate, carbonate, or similar physiologically-acceptable counter-ion salt.

In a further particular embodiment, the compound of formula (I) is a salt.

In a further particular embodiment, the compound of formula (I) is in the form of the hydrochloride salt.

The compounds of formula (1) may be prepared by methods well known to the art.

In particular, the compounds of formula (I) may be prepared in one step by reacting an appropriately ortho-substituted nitrogen-bearing heterocycle and an appropriately substituted phenylthiol; as shown in the following reaction schemes:

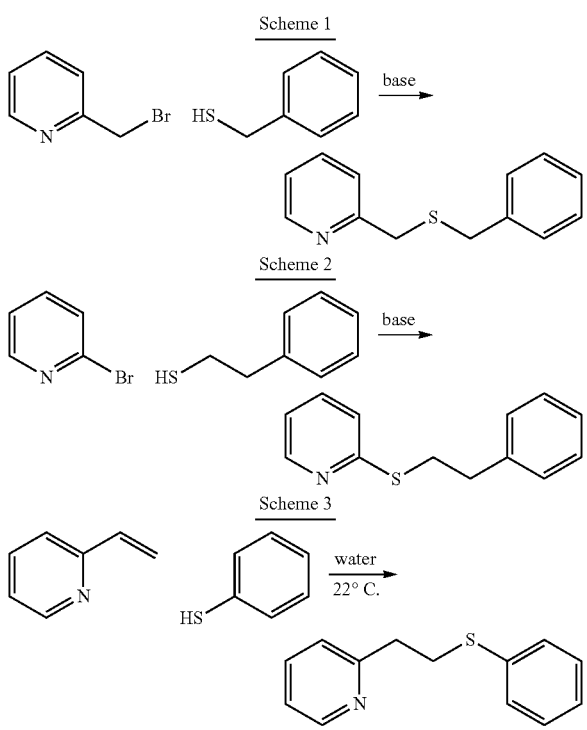

Other examples of suitable generally-applicable methods are described in, for example, Profft in *Monatsberichte der Deutschen Akademie der Wissenschaften zu Berlin*, 1 (1959), No. 11, 694-6, Profft in *Wissentschaftliche Zeitschrift der Technischen Hochschule für Chemie "Carl Schorlemmer" Leuna-Merseburg* (1960) 101-2, Bentley et al in WO 2011/138266 and Tagaki et al in JP 2000-351767.

Further details of suitable synthesis routes to the compounds of formula (I) are set forth in the examples, described below.

The reaction conditions, that is, the choice of solvent, temperature, pH and the like, appropriate for affecting the chemical syntheses described above are well known in the art and require no further elaboration here. Particular reaction conditions are set forth in the examples below.

Some of the compounds prepared as hereinabove described are novel compounds. There is therefore also provided a compound of the formula I, or the hydrochloride salt thereof, in which $X_1$ and $X_2$ are $CH_2$, $X_3$ is sulfur and A is a mono-substituted phenyl, the substituent being selected from $CH_3$, OH, $OCH_3$ COOH, $COOR_7$, in which $R_7$ is selected from linear or branched $C_1$-$C_7$ alkyl, and $CONR_7R_8$, in which $R_8$ and $R_9$ are independently selected from hydrogen and straight or branched $C_1$-$C_4$ alkyl.

It has also been found that the compounds of formula (I) may impart, or modify one or more other olfactory, gustatory or trigeminal flavour sensations e.g. aroma, taste and mouth feel.

In particular it has been found that the compound of formula (I), as defined herein, may be used to impart to, or modify in, a flavour composition or comestible product, salt taste, fruity, green, green pepper, tomato and/or bell pepper aroma, and/or kokumi sensation.

In an particular embodiment, there is provided a method of imparting to, or modifying in, a flavour composition or comestible product, salt taste, comprising the addition to said flavour composition or comestible product of at least one compound of formula (I) as defined herein.

In a further particular embodiment, there is provided a method of imparting to, or modifying in, a flavour composition or comestible product, a fruity, green, green pepper, tomato and/or bell pepper aroma, comprising the addition to said flavour composition or comestible product of at least one compound of formula (I) as defined herein.

In a further particular embodiment, there is provided a method of imparting to, or modifying in, a flavour composition or comestible product, the kokumi sensation, comprising the addition to said flavour composition or comestible product of at least one compound of formula (I) as defined herein.

The term "Kokumi sensation" is a term used in the flavour industry to describe characteristics such as salivating, continuity, mouthfulness, richness and thickness.

The term "modify" as used herein refers to the ability of a compound of formula (I) to alter the perception of one or more olfactory, gustatory, or trigeminal flavour sensation e.g. aroma, taste and/or mouthfeel.

The compounds of formula (I) may alter the perception of one or more olfactory, gustatory, or trigeminal flavour sensation temporally, or by altering the quality or intensity for example by enhancing, strengthening, softening or sharpening.

The temporal profile of a taste or flavour includes three aspects, the very first taste or flavour sensation ("initial impact"), the medium taste or flavour sensation ("body"), and the time period during which taste or flavour lasts or lingers ("lingering period"). Typically the 'initial impact' lasts from 0 to 5 seconds, the 'body' lasts between 5 to 20 seconds, and the 'lingering period' lasts from 20 seconds onwards.

The compounds of formula (I) may be added into a composition in neat form, or they may first be modified, for example they may be entrapped or encapsulated with an entrapment or encapsulation material such as for example polymers, capsules, microcapsules, nanocapsules, liposomes, precursors, film formers, absorbents such as for example by using carbon or zeolites, cyclic oligosaccharides and mixtures thereof, or they may be chemically bound to substrates which are adapted to release the compounds of formula (I) upon application of an exogenous stimulus such as light, enzymes, or the like. The compounds of formula (I) may be modified in order to achieve a desired technical effect such as to achieve stability or to effect controlled release.

In a further particular embodiment, there is provided a flavour composition or comestible product comprising at least one compound of formula I as defined herein.

A compound of formula (I) may be the sole flavouring component in a flavour composition or comestible product or, a compound of formula (I) may be used in conjunction with other compounds of formula (I) and/or additional flavour ingredients.

Additional flavour ingredients may be selected from natural flavours, artificial flavours, spices, seasonings, and the like, synthetic flavour oils and flavouring aromatics and/or oils, oleoresins, essences, distillates, and extracts derived from plants, leaves, flowers, fruits, and so forth, Generally, any flavouring or food additive such as those described in Chemicals Used in Food Processing, publication 1274, pages 63-258, by the National Academy of Sciences, can be used.

Particular examples of other umami compounds that may be employed as additional flavour ingredients include the compounds described in International Publication No. WO12011/004016. Other non-limiting examples of umami flavour-conferring and -enhancing compounds include those described in EP 1642886, WO 2005/015158, EP 1312268, WO 2003/088768, EP 1291342 and WO 2006/003107.

A compound of formula (I) can additionally be used in flavour compositions or comestible products, as described hereinabove, in conjunction with one or more ingredients or excipients conventionally used in flavour compositions or comestible products, for example carrier materials and other auxiliary agents commonly used in the art. Suitable excipients for flavour compositions and comestible products are well known in the art and include, for example, without limitation, solvents (including water, alcohol, ethanol, oils, fats, vegetable oil, and miglyol), binders, diluents, disintegranting agents, lubricants, flavouring agents, coloring agents, preservatives, antioxidants, emulsifiers, stabilisers, flavour-enhancers, anti-caking agents, and the like.

Examples of such carriers or diluents for flavour compositions and comestible products may be found in for example, "Perfume and Flavour Materials of Natural Origin", S. Arctander, Ed., Elizabeth, N.J., 1960; in "Perfume and Flavour Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

Other suitable and desirable ingredients of flavour compositions and comestible products are described in standard texts, such as "Handbook of Industrial Chemical Additives", ed. M. and I. Ash, $2^{nd}$ Ed., (Synapse 2000).

The compounds of formula (I) may be used in a flavour composition at a concentration of up to 100% by weight of the flavour ingredients. However, more commonly compounds of formula (I) will be used with additional flavour ingredients at a concentration of 0.01% to 99.9% by weight of the flavour components of the flavour composition.

The concentration in which a compounds of formula (I) may be added to comestible products may vary within wide limits and depend, inter alia, on the nature of the comestible product, on the effect desired, the purpose of adding compounds of formula (I) to a comestible product, for example imparting or enhancing a umami taste, and on the nature and quantity of any other components of the consumable product.

Non-limiting exemplary concentrations of compounds of formula (I), in ppm by weight based on the weight of the comestible product, may be: 500 ppm to 0.01 ppm, more particularly 250 ppm to 0.01 ppm, still more particularly 100 ppm to 1 ppm.

A compound of formula (I), or flavour compositions comprising at least one compound of formula (I), may be added to comestible products by using conventional techniques to directly admix said compounds or compositions into the comestible product.

The use of the compounds of formula (I) in flavour compositions and comestible products enables the levels of other umami taste-imparting or modifying ingredients e.g. MSG and ribonucleotides such as disodium inosinate, and disodium guanylate (typically added to MSG as enhancers at low MSG levels), ordinarily present in flavour compositions and comestible products, to be reduced.

It is customary to employ MSG in such amounts such that, when a flavour composition is added to a comestible product, the MSG is present in amounts of between about 200 to 500 ppm. In reduced MSG comestible products, the amount of MSG is usually a lower amount in the range of about 100 to 200 ppm. In the case of ribonucleotides, the proportion may be from about 5 to ppm.

Compounds of formula (I) may be used to reduce up to 99.9% of the MSG or ribonucleotides in a flavour composition or comestible product. However, more commonly compounds of formula (I) will be used to reduce 10-35%, 10-25%, of the MSG, or ribonucleotides in a flavour composition or comestible product.

The term "comestible product(s)" refers to any composition that is put in the mouth and consumed, or that is placed in the mouth to achieve an effect before being discarded. By "comestible product base" is meant all the ingredients that make up a comestible product, apart from the compounds of formula (I). All of the standard ingredients known to the art may be employed in art-recognised quantities and the person skilled in the art will either know what can be used in every situation, or can find this by routine, non-inventive experimentation. These include, but are not limited to, anti-caking agents, anti-foaming agents, anti-oxidants, binders, colourants, diluents, disintegrants, emulsifiers, encapsulating agents or formulations, enzymes, fats, flavour-enhancers, flavouring agents, gums, lubricants, polysaccharides, preservatives, proteins, solubilisers, solvents, stabilisers, sugar-derivatives, surfactants, sweetening agents, vitamins, waxes, and the like. Solvents which may be used are known to those skilled in the art and include e.g. ethanol, ethylene glycol, propylene glycol, glycerine and triacetin. Encapsulants and gums include maltodextrin, gum arabic, alginates, gelatine, modified starch, and polysaccharides. Examples of additives, excipients, carriers, diluents or solvents for flavour or fragrance compounds may be found e.g. in "Perfume and Flavour Materials of Natural Origin", S. Arctander, Ed., Elizabeth, N.J., 1960; in "Perfume and Flavour Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

The compounds of formula (I) can be added to all manner of comestible products.

Examples include, but are not limited to, foodstuffs of all kinds, confectionery products, baked products, sweet products, savory products, dairy products, beverages and oral care products.

Exemplary foodstuffs include, but are not limited to, chilled snacks, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, dried food, dessert mixes, sauces, dressings and condiments, herbs and spices, spreads, jams and preserves, honey, chocolate spreads, nut-based spreads, and yeast-based spreads.

Exemplary confectionery products include, but are not limited to, chewing gum (which includes sugarized gum, sugar-free gum, functional gum and bubble gum), centerfill confections, chocolate and other chocolate confectionery, medicated confectionery, lozenges, tablets, pastilles, mints, standard mints, power mints, chewy candies, hard candies, boiled candies, breath and other oral care films or strips, candy canes, lollipops, gummies, jellies, fudge, caramel, hard and soft panned goods, toffee, taffy, liquorice, gelatin candies, gum drops, jelly beans, nougats, fondants, combinations of one or more of the above, and edible compositions incorporating one or more of the above.

Exemplary baked products include, but are not limited to, alfajores, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, and bread substitutes.

Exemplary sweet products include, but are not limited to, breakfast cereals, ready-to-eat ("rte") cereals, family breakfast cereals, flakes, muesli, other rte cereals, children's breakfast cereals, and hot cereals.

Exemplary savory products include, but are not limited to, salty snacks (potato chips, crisps, nuts, tortilla-tostada, pretzels, cheese snacks, corn snacks, potato-snacks, ready-to-eat popcorn, microwaveable popcorn, pork rinds, nuts, crackers, cracker snacks, breakfast cereals, meats, aspic, cured meats (ham, bacon), luncheon/breakfast meats (hotdogs, cold cuts, sausage), tomato products, margarine, peanut butter, soup (clear, canned, cream, instant, UHT), canned vegetables, and pasta sauces.

Exemplary dairy products include, but are not limited to, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavoured, functional and other condensed milk, flavoured milk drinks, dairy only flavoured milk drinks, flavoured milk drinks with fruit juice, soy milk, sour milk drinks, fermented dairy drinks, coffee whiteners, powder milk, flavoured powder milk drinks, cream, yoghurt, plain/natural yoghurt, flavoured yoghurt, fruited yoghurt, probiotic yoghurt, drinking yoghurt, regular drinking yoghurt, probiotic drinking yoghurt, chilled and shelf-stable desserts, dairy-based desserts, and soy-based desserts.

Exemplary beverages include, but are not limited to, flavoured water, soft drinks, fruit drinks, coffee-based drinks, tea-based drinks, juice-based drinks (includes fruit and vegetable), milk-based drinks, gel drinks, carbonated or non-carbonated drinks, powdered drinks, alcoholic or non-alcoholic drinks.

There now follows a series of non-limiting illustrative examples.

EXAMPLE 1:
2-(2-(PHENYLTHIO)ETHYL)PYRIDINE
(CAS: 21070-71-3)

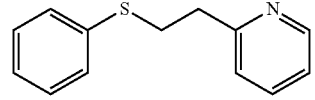 [SMILES: c1ccc(SCCc2ccccn2)cc1]

Benzenethiol (4.66 ml, 45.4 mmol) was added to Water (20 ml) followed by 2-vinylpyridine (4.89 ml, 45.4 mmol) and the contents were stirred overnight at room temperature (rt). The next day the product was extracted with ethyl acetate (100 ml). The organic layer was dried ($Na_2SO_4$), filtered and concentrated providing an oil. The crude oil was purified by column chromatography on $SiO_2$ using a gradient of 100% hexane to 50:50 hexane:EtOAc providing the desired 2-(2-(phenylthio)ethyl)pyridine (8.2 g, 84% yield) as a clear oil. $^1$H NMR (300 MHz, $d_6$-DMSO, ppm) δ 3.019 (t, J=7 Hz, 2H), 3.34 (t, J=7 Hz, 2H), 7.08-7.40 (m, 7H), 7.66-7.71 (m, 1H), 8.49-8.51 (m, 1H); $^{13}$C NMR (75 MHz, $d_6$-DMSO, ppm) δ 31.5, 36.8, 121.6, 123.1, 125.6, 128.0, 129.0, 136.1, 136.4, 149.0, 159.2; GC/MS calculated for $C_{13}H_{13}NS$ 215, observed 215.

EXAMPLE 2:
2-(2-(PHENYLTHIO)ETHYL)PYRIDINE
HYDROCHLORIDE (CAS: 21070-72-4)

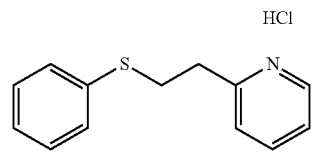 [SMILES: Cl ; c1ccc(SCCc2ccccn2)cc1]

A portion of 2-(2-(phenylthio)ethyl)pyridine from example 1 was dissolved in ether and treated with HCl gas resulting in a sticky oil. Scratching the walls of the vial with a metal spatula induced crystallization providing the desired 2-(2-(phenylthio)ethyl)-pyridine hydrochloride as a white solid. The ether was removed by filtration and the white solid was dried overnight in a vacuum oven at 40° C. $^1$H NMR (300 MHz, $d_6$-DMSO, ppm) δ 3.38 (t, J=7 Hz, 2H), 3.50-3.55 (m, 2H), 7.16-7.22 (m, 1H), 7.27-7.39 (m, 4H), 7.84-7.89 (m, 1H), 7.96 (d, J=8 Hz, 1H), 8.75-8.78 (m, 1H); $^{13}$C NMR (75 MHz, $d_6$-DMSO, ppm) δ 30.7, 32.6, 124.9, 126.0, 127.3, 128.4, 129.1, 134.9, 141.5, 145.2, 154.6.

EXAMPLE 3: METHYL 4-((2-(PYRIDIN-2-YL)
ETHYL)THIO)BENZOATE HYDROCHLORIDE
(CAS: 298217-38-6)

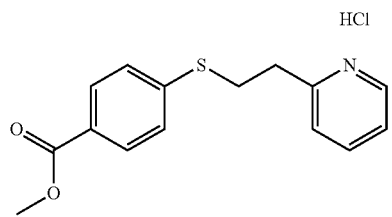 [SMILES: Cl ; COC(=O)c1ccc(SCCc2ccccn2)cc1]

Methyl 4-mercaptobenzoate (1 g, 5.94 mmol) was added to a 20 ml vial followed by Water (2.62 ml) and 2-vinylpyridine (0.641 ml, 5.94 mmol). The mixture was stirred overnight. The next day, the reaction mixture was diluted with ethyl acetate (10 ml) and passed through a Chem Elut extraction cartridge (Varian). The cartridge was washed several times with EtOAc. The dried theyl acetate and rinsings were collected in a 100 ml round bottom flask. The solvent was concentrated producing a crude cream colored solid. A TLC on silica gel using 50:50 hexane:EtOAc showed a single spot with an Rf of ~0.8. The solid was dissolved in dichloromethane and chromatographed on $SiO_2$ using a gradient of 100% hexane to 50:50 hexane:EtOAc. The product containing fractions were concentrated and the purified product was dissolved in ether and HCl gas was bubbled through. This generated a white, sticky oil that solidified into a white solid, when the vial was scratched with a spatula. The white solid was dried overnight at 40° C. in a vacuum oven providing the desired methyl 4-((2-(pyridin-2-yl)ethyl)thio)benzoate hydrochloride as a white solid (1.53 g, 83% yield). $^1$H NMR (300 MHz, $d_6$-DMSO, ppm) δ 3.43 (t, J=7 Hz, 2H), 3.62 (t, J=7 Hz, 2H), 3.83 (s, 3H), 7.47-7.51 (m, 2H), 7.83-7.91 (m, 3H), 8.00 (d, J=8 Hz, 1H), 8.47 (td, $J_1$=8 Hz, $J_2$=2 Hz, 1H), 8.78-8.80 (m, 1H); $^{13}$C NMR (75 MHz, $d_6$-DMSO, ppm) δ 29.4, 32.3, 52.0, 125.0, 126.3, 126.5, 127.3, 129.6, 141.6, 142.5, 145.3, 154.4, 165.8; GC/MS (Free base) calculated for $C_{15}H_{15}NO_2S$ 273, observed 273.

EXAMPLE 4: 2-(2-(P-TOLYLTHIO)ETHYL) PYRIDINE HYDROCHLORIDE (CAS: 109845-78-5)

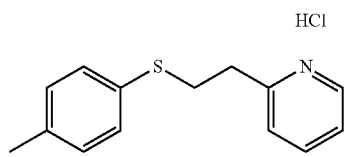 [SMILES: Cl ; Cc1ccc(SCCc2ccccn2)cc1]

4-Methylbenzenethiol (0.738 g, 5.94 mmol) was added to a 20 ml vial followed by Water (2.62 ml) and 2-vinylpyridine (0.641 ml, 5.94 mmol). The mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude cream colored solid. A TLC on silica gel using 50:50 hexane:EtOAc showed a single spot with an Rf of ~0.8. The solid was dissolved in dichloromethane and chromatographed on $SiO_2$ using a gradient of 100% hexane to 50:50 hexane:EtOAc. The resulting product was dissolved in ether and treated with HCl gas. This produced, after scratching with a spatula and vacuum oven drying at 40° C., the desired 2-(2-(p-tolylthio)-ethyl)pyridine hydrochloride as a white solid (1.26 g, 80% yield). $^1$H NMR (300 MHz, $d_6$-DMSO, ppm) δ 2.26 (s, 3H), 3.30-3.35 (m, 2H), 3.44-3.49 (m, 2H), 7.11-7.14 (m, 2H), 7.26-7.30 (m, 2H), 7.84-7.89 (m, 1H), 7.93 (d, J=8 Hz, 1H), 8.44 (td, $J_1$=8 Hz, $J_2$=2 Hz, 1H), 8.74-8.77 (m, 1H); $^{13}$C NMR (75 MHz, $d_6$-DMSO, ppm) δ 20.5, 31.4, 32.8, 124.9, 127.3, 129.3, 129.8, 131.1, 135.8, 141.6, 145.2, 154.7; GC/MS (Free base) calculated for $C_{14}H_{15}NS$ 229, observed 229.

EXAMPLE 5: 2-(2-(O-TOLYLTHIO)ETHYL) PYRIDINE HYDROCHLORIDE (CAS: 109846-70-0)

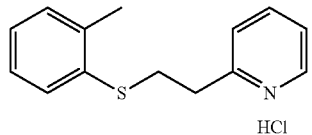 [SMILES: Cc1ccccc1SCCc1ccccn1 ; Cl]

2-Methylbenzenethiol (1 g, 8.05 mmol) was added to a 20 ml vial followed by Water (3.5 ml) and 2-vinylpyridine (0.846 g, 8.05 mmol). The mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude cream colored solid. A TLC on silica gel using 50:50 hexane:EtOAc showed a single spot with an Rf of ~0.8. The solid was dissolved in dichloromethane and chromatographed on $SiO_2$ using a gradient of 100% hexane to 50:50 hexane:EtOAc. The resulting product was dissolved in ether and treated with HCl gas. This produced, after scratching with a spatula and vacuum oven drying at 40° C., the desired 2-(2-(p-tolylthio)-ethyl)pyridine hydrochloride as a white solid (1.19 g, 56% yield). $^1$H NMR (300 MHz, $d_6$-DMSO, ppm) δ 2.24 (s, 3H), 3.34-3.40 (m, 2H), 3.47-3.53 (m, 2H), 7.09-7.14 (m, 1H), 7.17-7.21 (m, 2H), 7.40-7.43 (m, 1H), 7.81-7.86 (m, 1H), 7.93 (d, J=8 Hz, 1H), 8.41 (td, $J_1$=8 Hz, $J_2$=2 Hz, 1H), 8.75-8.78 (m, 1H); $^{13}$C NMR (75 MHz, $d_6$-DMSO, ppm) δ 19.8, 30.2, 32.8, 124.7, 125.7, 126.6, 126.9, 127.5, 130.1, 134.3, 136.4, 142.1, 144.6, 155.0; GC/MS (Free base) calculated for $C_{14}H_{15}NS$ 229, observed 229.

EXAMPLE 6: 4-((2-(PYRIDIN-2-YL)ETHYL) THIO)PHENOL (CAS: 1183541-70-9)

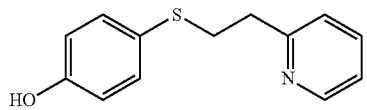 [SMILES: Oc1ccc(SCCc2ccccn2)cc1]

4-Mercaptophenol (0.749 g, 5.94 mmol) was added to Water (2.62 ml) followed by 2-vinylpyridine (0.641 ml, 5.94 mmol) and the mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude oil. The crude oil was dissolved in dichloromethane and chromatographed on $SiO_2$ using a gradient of 100% hexane to 80:20 hexane:EtOAc providing the desired product (1.07 g, 78% yield) as a white solid. $^1$H NMR (300 MHz, $d_6$-DMSO, ppm) δ 2.92 (t, J=7 Hz, 2H), 3.13-3.36 (m, 2H), 6.73-6.78 (m, 2H), 7.18-7.27 (m, 4H), 7.68 (td, $J_1$=8 Hz, $J_2$=2 Hz, 1H), 8.46-8.48 (m, 1H), 9.57 (s, 1H); $^{13}$C NMR (75 MHz, $d_6$-DMSO, ppm) δ 34.3, 37.2, 116.1, 121.5, 123.1, 123.4, 133.0, 136.4, 149.0, 156.8, 159.4; GC/MS calculated for $C_{13}H_{13}NOS$ 231, observed 231.

EXAMPLE 7: 2-((2-(PYRIDIN-2-YL)ETHYL)THIO)PHENOL (CAS: 1247529-36-7)

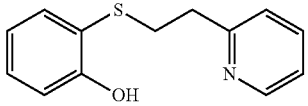 [SMILES: Oc1ccccc1SCCc1ccccn1]

2-Mercaptophenol (0.749 g, 5.94 mmol) was added to Water (2.62 ml) followed by 2-vinylpyridine (0.641 ml, 5.94 mmol) and the mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude oil. The crude oil was dissolved in dichloromethane and chromatographed on $SiO_2$ using a gradient of 100% hexane to 80:20 hexane:EtOAc providing the desired product (1.15 g, 84% yield) as a white solid. $^1$H NMR (300 MHz, $d_6$-DMSO, ppm) δ 2.98 (t, J=7 Hz, 2H), 3.19-3.25 (m, 2H), 6.77-6.85 (m, 2H), 7.03-7.08 (m, 1H), 7.20-7.30 (m, 3H), 7.71 (td, $J_1$=8 Hz, $J_2$=2 Hz, 1H), 8.49-8.51 (m, 1H), 9.83 (s, 1H); $^{13}$C NMR (75 MHz, $d_6$-DMSO, ppm) 30.7, 36.8, 115.0, 119.6, 121.58, 121.6, 123.1, 127.1, 129.6, 136.5, 148.9, 155.5, 159.4; GC/MS calculated for $C_{13}H_{13}NOS$ 231, observed 231.

EXAMPLE 8: 2-(2-((3-METHOXYPHENYL)THIO)ETHYL)PYRIDINE

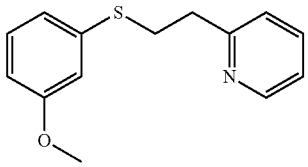 [SMILES: COc1cccc(SCCc2ccccn2)c1]

3-Methoxybenzenethiol (0.833 g, 5.94 mmol) was added to Water (2.62 ml) followed by 2-vinylpyridine (0.641 ml, 5.94 mmol) and the mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude oil. The crude oil was dissolved in dichloromethane and chromatographed on $SiO_2$ using a gradient of 100% hexane to 80:20 hexane:EtOAc providing the desired product (1.14 g, 78% yield) as a clear oil. $^1$H NMR (300 MHz, $d_6$-DMSO, ppm) δ 3.03 (t, J=7 Hz, 2H), 3.32-3.37 (m, 2H), 3.75 (s, 3H), 6.75 (ddd, $J_1$=8 Hz, $J_2$=2 Hz, 1 Hz, 1H), 6.87-6.92 (m, 2H), 7.20-7.30 (m, 3H), 7.70 (ddd, $J_1$=8 Hz, $J_2$=2 Hz, 1H), 8.49-8.51 (m, 1H); $^{13}$C NMR (75 MHz, $d_6$-DMSO, ppm) 31.3, 36.8, 55.1, 111.4, 113.0, 119.9, 121.6, 123.1, 129.9, 136.4, 137.5, 149.0, 159.2, 159.6; GC/MS calculated for $C_{14}H_{15}NOS$ 245, observed 245.

EXAMPLE 9: METHYL 2-((2-(PYRIDIN-2-YL)ETHYL)THIO)BENZOATE HYDROCHLORIDE

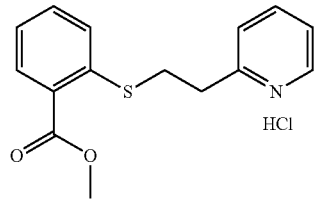 [SMILES: COC(=O)c1ccccc1SCCc1ccccn1 ; Cl]

Methyl 2-mercaptobenzoate (0.999 g, 5.94 mmol) was added to Water (2.62 ml) followed by 2-vinylpyridine (0.641 ml, 5.94 mmol) and the mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude oil. The crude oil was dissolved in dichloromethane and chromatographed on $SiO_2$ using a gradient of 100% hexane to 50:50 hexane:EtOAc. The resulting product was dissolved in ether and treated with HCl gas. This produced, after scratching with a spatula and vacuum oven drying at 40° C., the desired product as a white solid (1.45 g, 79% yield). $^1$H NMR (300 MHz, $d_6$-DMSO, ppm) δ 3.41-3.56 (m, 4H), 3.82 (s, 3H), 7.25-7.31 (m, 1H), 7.55-7.66 (m, 2H), 7.86-7.93 (m, 2H), 8.03 (d, J=8 Hz, 1H), 8.50 (ddd, $J_1$=8 Hz, $J_2$=2 Hz, 1H), 8.80-8.82 (m, 1H); $^{13}$C NMR (75 MHz, $d_6$-DMSO, ppm) δ 29.6, 31.8, 52.1, 124.5, 125.0, 126.3, 127.3, 127.6, 130.7, 132.8, 139.2, 141.5, 145.5, 154.6, 166.0; GC/MS (Free base) calculated for C15H15NO2S 273, observed 273.

EXAMPLE 10: 3-((2-(PYRIDIN-2-YL)ETHYL)THIO)PHENOL

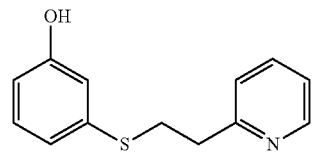 [SMILES: Oc1cccc(SCCc2ccccn2)c1]

3-mercaptophenol (0.749 g, 5.94 mmol) was added to Water (2.62 ml) followed by 2-vinylpyridine (0.641 ml, 5.94 mmol) and the mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude oil. The crude oil was dissolved in dichloromethane and chromatographed on $SiO_2$ using a gradient of 100% hexane to 80:20 hexane:EtOAc providing the desired product (0.82 g, 60% yield) as a clear oil.

$^1$H NMR (300 MHz, $d_6$-DMSO, ppm) δ 3.02 (t, J=7 Hz, 2H), 3.27-3.32 (m, 2H), 6.57-6.61 (m, 1H), 6.74-6.77 (m, 2H), 7.08-7.14 (m, 1H), 7.19-7.29 (m, 2H), 7.70 (ddd, $J_1$=8 Hz, $J_2$=2 Hz, 1H), 8.49-8.51 (m, 1H), 9.53 (s, 1H); $^{13}$C NMR (75 MHz, $d_6$-DMSO, ppm) δ 31.4, 36.8, 112.8, 114.5, 118.5, 121.6, 123.1, 129.9, 136.4, 137.0, 149.0, 157.8, 159.2; GC/MS calculated for $C_{13}H_{13}NOS$ 231, observed 231.

EXAMPLE 11: 2-(2-(BENZYLTHIO)ETHYL)PYRIDINE (CAS: 31932-68-0)

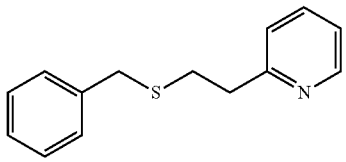 [SMILES: c1ccc(CSCCc2ccccn2)cc1]

Phenylmethanethiol (0.697 ml, 5.94 mmol) was added to Water (2.62 ml) followed by 2-vinylpyridine (0.641 ml, 5.94 mmol) and the mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude oil. The crude oil was dissolved in dichloromethane and chromatographed on $SiO_2$ using a gradient of 100% hexane to 80:20 hexane:EtOAc providing the desired product (0.76 g, 56% yield) as a clear oil.

$^1$H NMR (300 MHz, $d_6$-DMSO, ppm) δ 2.73-2.79 (m, 2H), 2.96 (t, J=7 Hz, 2H), 3.74 (s, 2H), 7.18-7.28 (m, 3H), 7.29-7.32 (m, 4H), 7.68 (ddd, $J_1$=8 Hz, $J_2$=2 Hz, 1H), 8.46-8.49 (m, 1H); $^{13}$C NMR (75 MHz, $d_6$-DMSO, ppm) δ 30.2, 35.0, 37.2, 121.5, 123.0, 126.7, 128.3, 128.8, 136.3, 138.6, 149.0, 159.7; GC/MS calculated for $C_{14}H_{15}NS$ 229, observed 229.

EXAMPLE 12: 2-(2-(M-TOLYLTHIO)ETHYL)PYRIDINE HYDROCHLORIDE

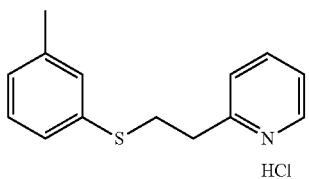 [SMILES: Cc1cccc(SCCc2ccccn2)c1 ; Cl]

3-Methylbenzenethiol (0.707 ml, 5.94 mmol) was added to water (2.62 ml) followed by 2-vinylpyridine (0.641 ml, 5.94 mmol) and the mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude oil. The crude oil was dissolved in dichloromethane and chromatographed on $SiO_2$ using a gradient of 100% hexane to 50:50 hexane:EtOAc. The resulting product was dissolved in ether and treated with HCl gas. This produced, after scratching with a spatula and vacuum oven drying at 40° C., the desired product as a white solid (0.93 g, 59% yield). $^1$H NMR (300 MHz, $d_6$-DMSO, ppm) δ 2.27 (s, 3H), 3.35-3.40 (m, 2H), 3.49-3.54 (m, 2H), 6.97-7.01 (m, 1H), 7.13-7.21 (m, 3H), 7.87 (ddd, $J_1$=7 Hz, $J_2$=6 Hz, $J_3$=1 Hz, 1H), 7.96 (d, J=8 Hz, 1H), 8.46 (ddd, $J_1$=8 Hz, $J_2$=1 Hz, 1H), 8.75-8.77 (m, 1H); $^{13}$C NMR (75 MHz, $d_6$-DMSO, ppm) δ 20.8, 30.7, 32.7, 125.0, 125.5, 126.8, 127.4, 128.9, 134.6, 138.5, 141.4, 145.4, 154.5; GC/MS (Free base) calculated for $C_{14}H_{15}NS$ 229, observed 229.

EXAMPLE 13: 2-(2-((4-METHOXYPHENYL)THIO)ETHYL)PYRIDINE HYDROCHLORIDE (CAS: 261360-83-2)

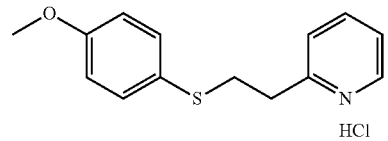 [SMILES: COc1ccc(SCCc2ccccn2)cc1 ; Cl]

4-Methoxybenzenethiol (0.833 g, 5.94 mmol) was added to Water (2.62 ml) followed by 2-vinylpyridine (0.641 ml, 5.94 mmol) and the mixture was stirred overnight. The next day, the reaction mixture was diluted with ethyl acetate (10 ml) and passed through a Chem Elut extraction cartridge (Varian). The cartridge was washed several times with EtOAc and the dried reaction and rinsings were collected in a 100 ml round bottom flask. The solvent was concentrated producing a crude oil. The crude oil was dissolved in dichloromethane and chromatographed on $SiO_2$ using a gradient of 100% hexane to 50:50 hexane:EtOAc. The resulting product was dissolved in ether and treated with HCl gas. This produced, after scratching with a spatula and vacuum oven drying at 40° C., the desired product as a white solid (0.64 g, 38% yield). $^1$H NMR (300 MHz, $d_6$-DMSO, ppm) δ 3.29-3.34 (m, 2H), 3.38-3.43 (m, 2H), 3.73 (s, 3H), 6.86-6.91 (m, 2H), 7.32-7.37 (m, 2H), 7.85-7.90 (m, 1H), 7.94 (d, J=8 Hz, 1H), 8.46 (ddd, $J_1$=8 Hz, $J_2$=1 Hz, 1H), 8.75-8.76 (m, 1H); $^{13}$C NMR (75 MHz, $d_6$-DMSO, ppm) δ 32.7, 32.9, 55.2, 114.8, 124.6, 125.0, 127.4, 132.5, 141.3, 145.4, 154.6, 158.5; GC/MS (Free base) calculated for $C_{14}H_{15}NOS$ 245, observed 245.

EXAMPLE 14: TASTE EVALUATION IN WATER

A one percent cut of each compound of Examples 1-13 was prepared first. The hydrochloride salts were cut directly into water, while the free base examples were cut into ethanol. Next, 100 ml of a 1 ppm, 10 ppm and 20 ppm solution were prepared. The 1 ppm standards were prepared by addition of 0.0126 ml (cut in ethanol) or 0.01 ml (cut in water) to an amber bottle followed by dilution to 100 g total sample weight using water. The 10 and 20 ppm solutions were prepared similarly, but using 0.126 ml ethanol/0.1 ml water or 0.252 ml ethanol/0.2 ml water of the 1% cuts respectively. Next, the samples were evaluated by a panel of trained tasters. The data from these taste sessions are presented in Table I.

TABLE I

Taste evaluation in water

| Ex. | Conc. (ppm) | taste | aroma |
|---|---|---|---|
| 1 | 1 | weak to moderate umami | green |
| 1 | 10 | moderate umami, very weak: bitter, very weak astringent, salty | green |
| 1 | 20 | strong umami, very weak bitter, weak metallic | Green, tomato, bell pepper |
| 2 | 1 | weak umami, very weak astringent | green |
| 2 | 10 | moderate umami, very weak: salty, bitter, metallic, astringent | green |
| 2 | 20 | moderate umami, weak: salty, bitter, astringent | green |
| 3 | 1 | weak to moderate umami, very weak: bitter, metallic, astringent | |
| 3 | 10 | moderate umami, weak: bitter, metallic, astringent, | bloody metallic |
| 3 | 20 | moderate to strong umami, weak: bitter, metallic | bloody metallic |
| 4 | 1 | very weak: umami, bitter, astringent | |
| 4 | 10 | weak: umami, bitter, astringent, very weak metallic | green |
| 4 | 20 | Weak: umami, bitter, metallic, sour, astringent | green |
| 5 | 1 | weak bitter, astringent, very weak metallic | green pepper |
| 5 | 10 | weak umami, very weak bitter | green pepper |
| 5 | 20 | weak umami, very weak: bitter, astringent | green pepper |
| 6 | 1 | very weak: umami, astringent | green |
| 6 | 10 | weak: umami, bitter, astringent, very weak metallic | Green, fruity |
| 6 | 20 | weak: umami, bitter, astringent, very weak metallic | Green, fruity |
| 7 | 1 | very weak: umami, salty, weak bitter | Green pepper |
| 7 | 10 | weak to moderate umami, weak: bitter, metallic, very weak salty, | Green pepper |
| 7 | 20 | Weak to moderate umami, weak bitter, very weak salty, metallic, astringent | Green pepper |
| 8 | 1 | very weak metallic, weak astringent | Green pepper, beany |
| 8 | 10 | weak: umami, astringent, very weak: bitter, metallic, | Green pepper |
| 8 | 20 | weak: umami, very weak: bitter, metallic | Green pepper |
| 9 | 1 | weak: umami, astringent, very weak: salty, bitter | |
| 9 | 10 | moderate umami,, weak: salty, astringent, very weak: bitter, metallic | |
| 9 | 20 | moderate umami, weak: salty, astringent, tingling, very weak: salivating, metallic | |
| 10 | 1 | very weak bitter | green |
| 10 | 10 | weak: umami, metallic, very weak: bitter, astringent | |
| 10 | 20 | weak: umami, astringent, bitter, very weak: salty, metallic | vegetable |
| 11 | 1 | weak umami, very weak astringent | phenolic |
| 11 | 10 | weak umami, very weak astringent | Phenolic, spicy |
| 11 | 20 | moderate to strong umami, very weak bitter, weak astringent | Phenolic, spicy |
| 12 | 1 | weak: umami, astringent, very weak salty | |
| 12 | 10 | moderate umami, weak: salty, astringent | |
| 12 | 20 | moderate to strong umami, weak: salty, astringent | |
| 13 | 1 | Weak umami, very weak bitter, astringent | |
| 13 | 10 | Moderate to strong umami, very weak: bitter, salty | |
| 13 | 20 | Strong umami, very weak bitter | pyrazine |

EXAMPLE 15: FLAVOR APPLICATION EXAMPLES

Umami evaluations were done in dry noodle seasoning, chicken broth, retorted chicken broth, cheese sauce and salted potato chip applications. Each application was prepared using MSG, the experimental umami tastant and a blank which contained neither MSG nor the experimental umami tastant. Next, using a bench-top tasting panel (consisting of 7 to 14 panelists), panelists were asked to record the sensory attribute differences between the control (blank), the MSG application and the application containing the experimental umami tastant. These sensory attributes include umami, saltiness, bitterness, off-notes, mouth feel attribute, lingering attribute and flavor profile differences.

Noodle Seasoning Broth

| Ingredient | % |
|---|---|
| Salt | 51.28 |
| Sugar | 11.49 |
| Citric acid | 0.1 |

-continued

| Ingredient | % |
| --- | --- |
| Palm fat | 1.54 |
| Turmeric powder | 0.21 |
| Whey powder | 15.38 |
| Maltodextrin (DE10) | 20.0 |
| TOTAL | 100 |

Turmeric was plated on salt and palm fat and blended well. Next, the remaining ingredients were added and mixed until well blended. A concentration of 1.5% of the resulting mixture in hot water generated the noodle seasoning broth.

The following three samples were tasted and compared.

| Ingredient | % (by weight) |
| --- | --- |
| Noodle Seasoning Broth | 100 |
| MSG | 0.1 |
| Noodle Seasoning Broth | Balance to 100 |
| Example 1 | 0.0001 |
| Noodle Seasoning Broth | Balance to 100 |

Sensory Findings:

The panelists ranked the umami strength of the noodle seasoning broth samples as follows: MSG>Example 1>Blank Noodle Seasoning. Some panelists noted a green pepper attribute in the Example 1 containing sample.

Number of panelists: 11

Number of panelists who noted green pepper offnote: 2

EXAMPLE 16: CHICKEN BROTH

| Name | Amount - base | Amount - tasting sample |
| --- | --- | --- |
| Chicken Fat | 10.12 g | 0.25 g |
| Salt | 18.21 g | 0.50 g |
| Onion powder | 0.81 g | 0.02 g |
| Ground turmeric | 0.04 g | 0.001 g |
| Chicken broth powder | 60.7 g | 1.50 g |
| Chicken broth powder | 10.1 g | 0.25 g |
| Water | — | 97.479 g |

Turmeric was plated on salt and chicken fat and blended well. Next, the remaining ingredients were added and mixed until well blended. A concentration of 2.5% of the resulting mixture in hot water (82° C. (180° F.)) generated the noodle seasoning broth.

| Ingredient | % (by weight) |
| --- | --- |
| Chicken Broth | 100 |
| MSG | 0.1 |
| Chicken Broth | Balance to 100 |
| Example 1 | 0.0002 |
| Chicken Broth | Balance to 100 |

Sensory Findings:

The panelists ranked the umami strength of the chicken broth samples as follows: MSG>Example 1>Blank Chicken Broth. Some panelists noted a green pepper/chili off-note attribute in the Example 1 containing sample.

Number of panelists: 11

Number of panelists who noted green pepper offnote: 3

EXAMPLE 17: RETORTED CHICKEN BROTH

The chicken broth generated in Example 16 was transferred to a can and sealed. Prior to sealing one batch was treated with the compound of Example 1 (0.0002% by weight) and the other batch was canned without the ingredient generating a blank control sample. After sealing the cans, they were heated to 121° C. (250° F.) (under pressure) for 25 minutes, cooled to room temperature and then stored in the refrigerator for two weeks. Prior to tasting, the cans were opened and reheated to 65.5° C. (150° F.).

| Ingredient | % (by weight) |
| --- | --- |
| Retorted Chicken Broth | 100 |
| Example 1 | 0.0002 |
| Retorted Chicken Broth | Balance to 100 |

Sensory Findings:

The panelists thought that the retorted chicken broth sample containing example 1 had more umami than the control but had pepper off-notes.

Number of panelists: 10

Number of panelists who noted green pepper offnote: 4

EXAMPLE 18: CHEESE SAUCE

| | Formula Weight | | |
| --- | --- | --- | --- |
| Ingredients | grams | lbs | % |
| Maltodextrin | 31.08 | 0.07 | 31.08% |
| MF Starch | 16.00 | 0.04 | 16.00% |
| Cheese Powder | 19.00 | 0.04 | 19.00% |
| Nonfat dry milk powder | 12.00 | 0.03 | 12.00% |
| Shortening Powder | 8.00 | 0.02 | 8.00% |
| Whey, Sweet | 6.00 | 0.01 | 6.00% |
| Salt, Fine | 2.70 | 0.01 | 2.70% |
| Cream Powder | 3.00 | 0.01 | 3.00% |
| Sodium Phosphate | 1.00 | 0.00 | 1.00% |
| KCL | 0.72 | 0.00 | 0.72% |
| Annatto, LQ | 0.20 | 0.00 | 0.20% |
| Citric Acid | 0.20 | 0.00 | 0.20% |
| Lactic Acid | 0.10 | 0.00 | 0.10% |
| TOTALS | 100.00 | 0.22 | 100.00% |

Annatto was plated on a mixture of salt, citric acid and lactic acid and blended well. Next, the remaining ingredients were added and mixed until well blended. The dry sauce mix was added to water to a concentration of 18% and cooked to boiling (100° C. (212° F.)).

| Ingredient | % (by weight) |
| --- | --- |
| Cheese Sauce | 100 |
| MSG | 0.1 |
| Cheese Sauce | Balance to 100 |
| Example 1 | 0.00025 |
| Cheese Sauce | Balance to 100 |

Sensory Findings:

The panelists ranked the umami strength of the cheese sauce samples as follows: MSG>Example 1>Blank Cheese Sauce. Some panelists noted a green pepper attribute in the Example 1 containing sample.

Number of panelists: 14
Number of panelists who noted green pepper offnote: 4

EXAMPLE 19: SALTED POTATO CHIPS

One percent salt was added to a standard unsalted potato chip.

| Ingredient | % (by weight) |
|---|---|
| 1% salted potato chips | 100 |
| MSG | 0.2 |
| 1% salted potato chips | Balance to 100 |
| Example 1 | 0.0001 |
| 1% salted potato chips | Balance to 100 |
| Example 1 | 0.0003 |
| 1% salted potato chips | Balance to 100 |

Sensory Findings:

The panelists ranked the umami strength of the potato chip samples as follows: MSG>3 ppm Example 1>1 ppm Example 1>Blank Salted Chips. Some panelists noted a peppery attribute in the Example 1 containing samples.

Number of panelists: 14
Number of panelists who noted green pepper offnote: 2

EXAMPLE 20: RETORTED CHICKEN BROTH

The procedure for the preparation of the retorted chicken broth is the same as in example 16. Compounds from Examples 3, 9, 10 and 13 were spiked individually into the chicken broth generating six samples, as described below.

| Ingredient | % (by weight) |
|---|---|
| Chicken Broth | 100 |
| MSG | 0.20 |
| Chicken Broth | Balance to 100 |
| Example 3 | 4 ppm |
| Chicken Broth | Balance to 100 |
| Example 13 | 3 ppm |
| Chicken Broth | Balance to 100 |
| Example 10 | 4 ppm |
| Chicken Broth | Balance to 100 |
| Example 9 | 3 ppm |
| Chicken Broth | Balance to 100 |

Sensory Findings:

The panelists ranked the umami strength of the chicken broth retort samples as follows: MSG>3 ppm example 9>3 ppm Example 13>4 ppm Example 3>Blank retorted chicken broth>4 ppm Example 10. Some panelists noted a sweeter flavor profile with a build up of umami character for example 3. Example 13 had a slightly sweet/slightly bitter profile. Example 10 had a green pepper aroma and was slightly bitter. Example 9 possessed a sweet, full umami profile.

Number of panelists: 9

EXAMPLE 21: BAIN MARIE (HOT WATER BATH) TEST WITH CHICKEN BROTH

Chicken broth was prepared as previously described in example 15. Compounds from Examples 3, 9, 10 and 13 were added to the chicken broth in the concentrations described below and placed in a hot water bath (150° F.) for 4 hours prior to taste evaluation.

| Ingredient | % (by weight) |
|---|---|
| Chicken Broth | 100 |
| MSG | 0.20 |
| Chicken Broth | Balance to 100 |
| Example 3 | 3 ppm |
| Chicken Broth | Balance to 100 |
| Example 13 | 2 ppm |
| Chicken Broth | Balance to 100 |
| Example 10 | 3 ppm |
| Chicken Broth | Balance to 100 |
| Example 9 | 2 ppm |
| Chicken Broth | Balance to 100 |

Sensory Findings:

The panelists ranked the umami strength of the Bain marie chicken broth samples as follows: MSG>2 ppm example 9>3 ppm Example 10=4 ppm Example 13>Blank chicken broth>3 ppm Example 3. Some panelists noted a bitter, limited umami flavor profile for example 3 in this application, while example 13 was described as mid/late umami with some late onset bitterness. Example 10 was described as having mid/late umami along with a slight bitterness and off notes. Example 9 was described as providing a boost in saltiness along with a strong, full umami taste profile.

Number of panelists: 7

EXAMPLE 22: SALTED POTATO CHIPS

The potato chips were prepared as previously described in example 19 and spiked with compounds from Examples 3, 9, 10 and 13 as described below.

| Ingredient | % (by weight) |
|---|---|
| 1% salted potato chips | 100 |
| MSG | 0.2 |
| 1% salted potato chips | Balance to 100 |
| Example 3 | 10 ppm |
| 1% salted potato chips | Balance to 100 |
| Example 13 | 10 ppm |
| 1% salted potato chips | Balance to 100 |
| Example 10 | 6 ppm |
| 1% salted potato chips | Balance to 100 |
| Example 9 | 10 ppm |
| 1% salted potato chips | Balance to 100 |

Sensory Findings:

The panelists ranked the umami strength of the potato chip samples as follows: 10 ppm Example 3>10 ppm Example 9>MSG>10 ppm Example 13>blank>6 ppm Example 10. Some panelists noted a slight to moderate level of umami along with strong salty profile for example 3. A good, salty, umami profile was described for example 13. Example 10 was described as having a nice salty, slight umami profile along with a slight offnote. Example 9 was described as better mouthfeel, slight to moderate umami with an overall clean profile.

Number of panelists: 9

Although the embodiments have been described in detail through the above description and the preceding examples, these examples are for the purpose of illustration only and it is understood that variations and modifications can be made by one skilled in the art without departing from the spirit and the scope of the disclosure. It should be understood that the embodiments described above are not only in the alternative, but can be combined.

The invention claimed is:

1. A method of imparting to, or modifying in, a comestible product, umami taste comprising
the addition to a comestible product base of at least one compound of formula (I)

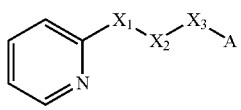

wherein one of $X_1$, $X_2$, or $X_3$ is selected from the group consisting of S, N and O and the remaining two are $CH_2$; and A is selected from

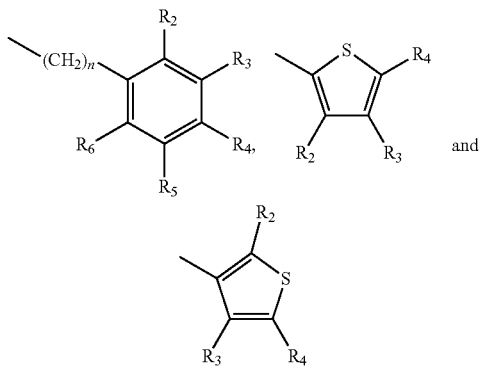

in which $R_2$, $R_3$, $R_4$, $R_5$, $R_6$ are independently selected from the group consisting of H, methyl, ethyl, propyl, OH, OMe, OEt, COOH, $COOR_7$, in which $R_7$ is selected from linear $C_1$-$C_7$ alkyl, branched $C_3$-$C_7$ alkyl, and $CONR_8R_9$, in which $R_8$ and $R_9$ are independently selected from hydrogen, straight $C_1$-$C_4$ alkyl, and branched $C_3$-$C_4$ alkyl; or any two adjacent substituents $R_2$-$R_6$ together form a ring of 5 or 6 members; and n is 1 or 0.

2. The method according to claim 1, in which one of $X_1$, $X_2$, or $X_3$ is S and the remaining two are $CH_2$.

3. The method according to claim 1, in which $X_1$ is S, and, $X_2$ and $X_3$ are $CH_2$.

4. The method according to claim 1, in which $X_2$ is S, and, $X_1$ and $X_3$ are $CH_2$.

5. The method according to claim 1, in which A is

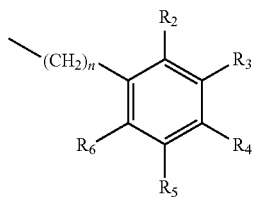

in which $R_2$, $R_3$, $R_4$, $R_5$, $R_6$ are independently selected from the group consisting of H, methyl, ethyl, propyl, OH, OMe, OEt, COOH, $COOR_7$, in which $R_7$ is selected from linear $C_1$-$C_7$ alkyl, branched $C_3$-$C_7$ alkyl, and $CONR_8R_9$, in which $R_8$ and $R_9$ are independently selected from hydrogen, straight $C_1$-$C_4$ alkyl, and branched $C_3$-$C_4$ alkyl; or any two adjacent substituents $R_2$-$R_6$ together form a ring of 5 or 6 members; and n is 1 or 0.

6. The method according to claim 1, in which $X_1$ is S, and, $X_2$ and $X_3$ are $CH_2$, and A is

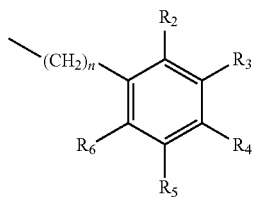

in which $R_2$, $R_3$, $R_4$, $R_5$, $R_6$ are independently selected from the group consisting of H, methyl, ethyl, propyl, OH, OMe, OEt, COOH, and $COOR_7$, in which $R_7$ is selected from linear $C_1$-$C_7$ alkyl and branched $C_3$-$C_7$ alkyl, and n is 0.

7. The method according to claim 1, in which the compound of formula (I) is selected from the group consisting of: 2-(2-(Phenylthio)ethyl)pyridine, 2-(2-(Phenylthio)ethyl)pyridine hydrochloride, Methyl 4-((2-(pyridin-2-yl)ethyl)thio) benzoate hydrochloride, 2-(2-(p-tolylthio)ethyl)pyridine hydrochloride, 2-(2-(o-tolylthio) ethyl)pyridine hydrochloride, 4-((2-(pyridin-2-yl)ethyl)thio)phenol, 2-((2-(pyridin-2-yl) ethyl)thio)phenol, 2-(2-((3-methoxyphenyl)thio)ethyl)pyridine, Methyl 2-((2-(pyridin-2-yl)ethyl)thio) benzoate hydrochloride, 3-((2-(pyridin-2-yl)ethyl)thio) phenol, 2-(2-(benzylthio)ethyl)pyridine, 2-(2-(m-Tolylthio) ethyl)pyridine hydrochloride, and 2-(2-((4-Methoxyphenyl)-thio)ethyl)pyridine hydrochloride.

8. The method according to claim 1, in which the compound of formula (I) is a salt.

9. The method according to claim 8, in which the compound of formula (I) is in the form of hydrochloride salt.

10. A method of imparting to, or modifying in, a flavour composition or comestible product, salt taste, comprising the addition to said flavour composition or comestible product of at least one compound of formula (I)

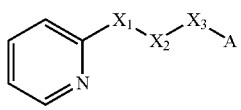

wherein one of $X_1$, $X_2$, or $X_3$ is selected from the group consisting of S, N and O and the remaining two are $CH_2$; and A is selected from

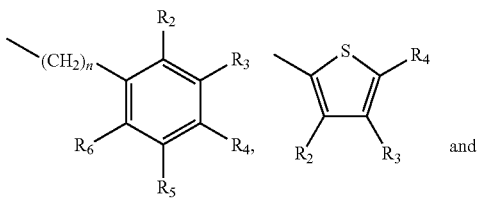

-continued

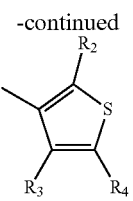

in which $R_2$, $R_3$, $R_4$, $R_5$, $R_6$ are independently selected from the group consisting of H, methyl, ethyl, propyl, OH, OMe, OEt, COOH, COOR$_7$, in which $R_7$ is selected from linear $C_1$-$C_7$ alkyl, branched $C_3$-$C_7$ alkyl, and CONR$_8$R$_9$, in which $R_8$ and $R_9$ are independently selected from hydrogen, straight $C_1$-$C_4$ alkyl, and branched $C_3$-$C_4$ alkyl; or any two adjacent substituents $R_2$-$R_6$ together form a ring of 5 or 6 members; and n is 1 or 0.

11. A method of imparting to, or modifying in, a flavour composition or comestible product, a fruity, green, green pepper, tomato and/or bell pepper aroma, comprising the addition to said flavour composition or comestible product of at least one compound of formula (I)

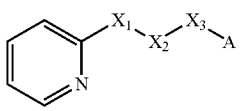

wherein one of $X_1$, $X_2$, or $X_3$ is selected from the group consisting of S, N and O and the remaining two are CH$_2$; and A is selected from

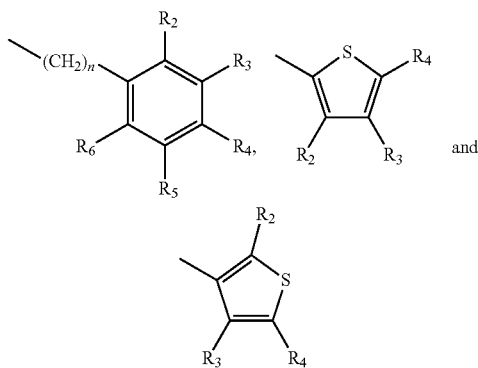

in which $R_2$, $R_3$, $R_4$ $R_5$, $R_6$ are independently selected from the group consisting of H, methyl, ethyl, propyl, OH, OMe, OEt, COOH, COOR$_7$, in which $R_7$ is selected from linear $C_1$-$C_7$ alkyl, branched $C_3$-$C_7$ alkyl, and CONR$_8$R$_9$, in which $R_8$ and $R_9$ are independently selected from hydrogen, straight $C_1$-$C_4$ alkyl, and branched $C_3$-$C_4$ alkyl; or any two adjacent substituents $R_2$-$R_6$ together form a ring of 5 or 6 members; and n is 1 or 0.

12. A method of imparting to, or modifying in, a flavour composition or comestible product, a kokumi sensation, comprising the addition to said flavour composition or comestible product of at least one compound of formula (I)

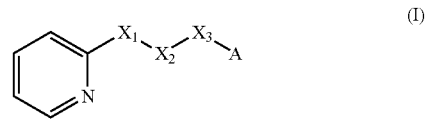

wherein one of $X_1$, $X_2$, or $X_3$ is selected from the group consisting of S, N and O and the remaining two are CH$_2$; and A is selected from

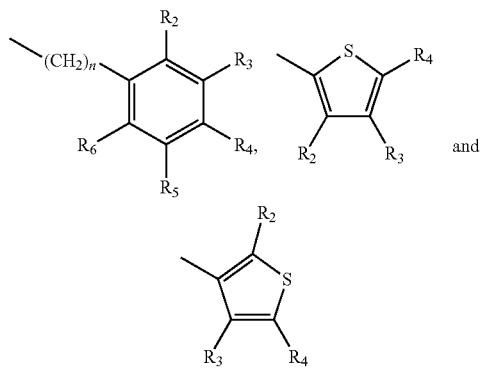

in which $R_2$, $R_3$, $R_4$ $R_5$, $R_6$ are independently selected from the group consisting of H, methyl, ethyl, propyl, OH, OMe, OEt, COOH, COOR$_7$, in which $R_7$ is selected from linear $C_1$-$C_7$ alkyl, branched $C_3$-$C_7$ alkyl, and CONR$_8$R$_9$, in which $R_8$ and $R_9$ are independently selected from hydrogen, straight $C_3$-$C_7$ alkyl, and branched $C_3$-$C_4$ alkyl; or any two adjacent substituents $R_2$-$R_6$ together form a ring of 5 or 6 members; and n is 1 or 0.

13. The method according to claim 1, in which the at least one compound of formula (I) is added in a concentration of from 0.01 ppm to 500 ppm by weight based on the weight of the comestible product.

14. The method according to claim 10, in which the at least one compound of formula (I) is added in a concentration of from 0.01 ppm to 500 ppm by weight based on the weight of the comestible product, or at a concentration of 0.01% to 99.9% by weight of flavour components of the flavour composition.

15. The method according to claim 11, in which the at least one compound of formula (I) is added in a concentration of from 0.01 ppm to 500 ppm by weight based on the weight of the comestible product, or at a concentration of 0.01% to 99.9% by weight of flavour components of the flavour composition.

16. The method according to claim 12, in which the at least one compound of formula (I) is added in a concentration of from 0.01 ppm to 500 ppm by weight based on the weight of the comestible product, or at a concentration of 0.01% to 99.9% by weight of flavour components of the flavour composition.

* * * * *